United States Patent [19]

Bobrow

[11] Patent Number: 5,391,479
[45] Date of Patent: Feb. 21, 1995

[54] METHOD FOR DETERMINING TOTAL ANALYTE CONCENTRATION IN A SAMPLE HAVING BOTH FREE AND BOUND ANALYTE

[75] Inventor: Mark N. Bobrow, Woburn, Mass.

[73] Assignee: E. I. Du Pont de Nemours and Company, Wilmington, Del.

[21] Appl. No.: 968,098

[22] Filed: Oct. 29, 1992

[51] Int. Cl.$^6$ .............................. C12Q 1/70
[52] U.S. Cl. ....................... 435/5; 435/7.1; 435/7.92; 435/7.93; 435/7.95; 435/961; 435/974; 436/506; 436/507; 436/538
[58] Field of Search ............. 436/500, 506, 507, 538; 435/7.93, 7.95, 974, 961, 7.92, 5, 7.1

[56] References Cited

U.S. PATENT DOCUMENTS

| Re. 31,006 | 8/1982 | Schuurs et al. | 435/7 |
|---|---|---|---|
| 4,098,876 | 7/1978 | Piasio et al. | 424/1 |
| 4,172,117 | 10/1979 | Schober | 424/1 |
| 4,200,690 | 4/1980 | Root et al. | 435/7 |
| 4,244,940 | 1/1981 | Jeong et al. | 424/1 |
| 4,604,348 | 8/1986 | Neurath | 435/7 |
| 4,703,001 | 10/1987 | Vodian et al. | 435/5 |
| 4,870,003 | 9/1989 | Kortright et al. | 435/5 |
| 4,877,725 | 10/1989 | Neurath et al. | 435/5 |
| 5,108,891 | 4/1992 | Croxson | 435/5 |

FOREIGN PATENT DOCUMENTS

| 0155104 | 2/1985 | European Pat. Off. | |
| WO-A-8810316 | 12/1988 | WIPO | G01N 33/53 |
| WO-A-8912233 | 12/1989 | WIPO | G01N 33/569 |
| WO-A-9008959 | 8/1990 | WIPO | G01N 33/569 |

OTHER PUBLICATIONS

Tijssen:Practice & Theory of Enzyme Immunoassays in *Laboratory Tech. in Biochemistry & Molecular Biology* V15 Elsever, New York, Burdon, ed. 1985.
McHugh et al J. Inf. Diseases, vol. 158, No. 5, Nov. 1988 pp. 1088–1091.
DuPont HIV-1 p 24 Acid Disruption Difference Kit.
Nishanian, P. et al., "A Simple Method for Improved Assay Demonstrates that HIV p24 Antigen Is Present as Immune Complexes in Most Sera from HIV–Infected Individuals," The Journal of Infectious Diseases, vol. 162, No. 1, Jul. 1990, pp. 21–28.
NEN Research Products, "HIV-1 p24 Core Profile Elisa-Simultaneous Detection of HIV-1 p24 Antigen/Antibody", pp. 1–27.
Yolken, "Solid phase immunoassays for the detection of viral diseases", Elsevier Science Publishers B.V., 1985, pp. 121–138.
von Sydow et al., "Antigen detection in primary HIV infection", British Medical Journal, vol. 296, Jan. 23, 1988, pp. 238–240.
Kageyama et al., "An improved method for the detection of HIV antigen in the blood of carriers", Journal of Virological Methods, 22(1988) 125–131.
Ekins, "Measurement of Free Hormones in Blood", Endocrines Reviews, vol. 11, No. 1, pp. 5–46.
Cohen, "Searching for Markers on the AIDS Trail", Science, vol. 258, Oct. 16, 1992, pp. 388–390.
McHugh et al., "Relation of Circulating Levels of Human . . . ", Journal of Infectious Diseases, vol. 158, No. 5, Nov. 1988, pp. 1088–1091.
Neurath et al., "Radioimmunoassays of hidden viarl antigens", Proc. Natl. Acad. Sci. USA, vol. 79, Jul. 1982, pp. 4415–4419.
Borkowsky et al., "Early Diagnosis of Human Immunodeficiency . . . ", JID 1992:166 (Sep.), pp. 616–619.
Nishanian et al., "A Simple Method for Improved Assay Demonstrates . . . ", JID 1990:162 (Jul.), pp. 21–28.

*Primary Examiner*—Christine M. Nucker
*Assistant Examiner*—Jeffrey Stucker

[57] ABSTRACT

A method for determining total analyte concentration in a sample having both free and bound analyte is described. This method involves (a) disassociating immune complexes, (b) assaying for the concentration of free analyte, (c) assaying at least once for the concentration of free analyte in the sample wherein said sample contains a known quantity of analyte which has been added to the sample, and (d) determining total analyte concentration from the assayed concentrations obtained in steps (b) and (c).

3 Claims, No Drawings

METHOD FOR DETERMINING TOTAL ANALYTE CONCENTRATION IN A SAMPLE HAVING BOTH FREE AND BOUND ANALYTE

FILED OF THE INVENTION

This invention relates to a method for determining the quantity of analyte in a sample and, more particularly, to method for determining total analyte concentration in a sample containing both free and bound analyte.

BACKGROUND OF THE INVENTION

Assays and, in particular, immunoassays are widely used as diagnostic tools in bacterial, viral and parasitic diseases as well as infectious diseases such as AIDS which constitute major health problems around the world.

Immunoassays are generally utilized for detecting and/or quantifying the amount of analyte in serum or other biological fluids and are based principally on the binding of specific binding substance, such as an antibody, to a particular analyte which might be present in a specimen. Unfortunately, detection of analyte is often hindered by the presence of endogenous binding substances because analyte is masked by the formation of endogenous binding substance-analyte complexes. For example, analytes such as Human Immunodeficiency Virus (HIV)-1 p24 core protein are present in serum, plasma, etc. bound in equilibrium to human antibody that has been produced as a consequence of viral infection. Masking by antibody (due to formation of antigen-antibody complexes) interferes with detection of analyte in a bound state by conventional methods such as enzyme-linked immunosorbent assay (ELISA) and radioimmunoassay (RIA). Consequently, only free analyte can be detected. However, determination of the amount of free analyte will be affected by a variety of factors such as the concentration of analyte, and the concentration and affinity of the antibody.

The inability of current methods to detect total concentration of analyte creates a serious problem where measurement of total analyte is important. For example, measurement of HIV antigen levels in sera or plasma of HIV-infected individuals is important in determining the existence of antigen or infectious virus before seroconversion and for prognosis and is a useful tool for monitoring antiviral drug therapy. Diagnosis of HIV infection in children during the first year of life is hampered by the inability of standard serologic assays to diagnose HIV due to persisting maternally derived antibody. Thus, to understand the role of HIV in the process of disease development, control and prognosis, reliable measurement of serum antigen and viral antigen production in HIV-infected individuals is very important.

Efforts to increase sensitivity and specificity of assay systems to improve detection and/or quantification of analyte have been undertaken as illustrated by the following:

U.S. Pat. No. 4,604,348, issued to Neurath on Aug. 5, 1986, describes a process for detecting antibodies or antigens in a sample where the antigens or antibodies are present in the form of an immune complex. This process involves irreversibly attaching the antigen or antibody to a protein sorbing solid support in the presence of a dissociating buffer. Once antigen or antibody derived from immune complex has been adsorbed to the solid support, the existence thereof can be determined by RIA or ELISA.

Similarly, Neurath et al., Proc. Natl. Acad. Sci. USA, 79: 4415-4419 (July 1982), describe a solid-phase method for separating antigens from antibodies. Specifically, immune complexes are precipitated from serum by polyethylene glycol, dissociated with NaSCN, and adsorbed onto nitrocellulose or polystyrene supports. Detection is then effected using RIA.

European Patent Application Publication No. 0 155 104 published Sep. 18, 1985 describes a free analyte assay in which analyte is present partly bound to natural protein binders and in which free analyte and an analyte derivative compete for reaction with a specific binder. A differential blocking agent is used to reduce binding of the analyte derivative but without reducing binding to analyte to natural protein binders.

U.S. Pat. No. 4,703,001, issued to Vodian et al. on Oct. 27, 1987, describes an immunoassay for detecting serum analytes using pH dependent chaotropic acids so that the analyte is substantially free from its antibody and/or other serum proteins are largely denatured.

Nishanian et al., J. Infect. Dis., 162: 21-28 (July 1990), von Sydow et al., Br. Med. J., 296: 238-240 (January 1988), and Kageyama et al., J. Virol. Meth., 22: 125-131 (1988), describe methods to enhance detection of HIV-1 antigen (present in immune complexes) in serum or plasma samples by pretreating samples at an acidic pH to dissociate immune complexes and denatured antibodies with little or no compromise of antigen immunoreactivity.

While these methods facilitate detection of undetectable or poorly detectable analytes, they do not provide for determination of total analyte concentration.

SUMMARY OF THE INVENTION

This invention relates to a method for determining total analyte concentration in a sample which comprises:

(a) assaying for the concentration of free analyte in the sample;

(b) assaying for the concentration of free analyte in the sample wherein said sample contains a known quantity of analyte which has been added to the sample, said determination being made at least once; and (c) determining total analyte concentration from the assayed concentrations obtained in steps (a) and (b).

In another embodiment this invention concerns, a method for determining total HIV antigen concentration in a sample which comprises:

(a) assaying for the concentration of free HIV antigen in the sample;

(b) assaying for the concentration of free HIV antigen in the sample wherein said sample contains a known quantity of analyte which has been added to the sample, said determination being made at least once; and (c) determining total HIV antigen concentration from the assayed concentrations obtained in steps (a) and (b).

DETAILED DESCRIPTION OF THE INVENTION

The method of this invention can be used to determine total analyte concentration in a sample which comprises:

(a) assaying for the concentration of free analyte in the sample;

(b) assaying for the concentration of free analyte in the sample wherein said sample contains a known quantity of analyte which has been added to the sample, said determination being made at least once; and (c) determining total analyte concentration from the assayed concentrations obtained in steps (a) and (b).

Any conventional assay used to detect and/or quantify free analyte in a biological sample such as plasma, serum, urine, etc. can be used in the method of the invention to provide a quick and precise determination of total analyte concentration in a biological sample containing analyte in both a free and bound form. If analyte does not exist in a free form, it can be rendered free using conventional techniques such as those described above. Examples of analytes which can be evaluated using the method of the invention include viral proteins, bacterial proteins, hormones, drugs, etc. In particular there can be mentioned blood-borne infectious agents such as HIV, hepatitis, Epstein-Barr virus, cytomegalovirus, HTLV-1, HTLV-II, etc.

An example of a commercially available assay which can be used is the Du Pont HIV-1 p24 Core Profile ELISA used in conjunction with the Du Pont HIV-1 p24 Acid Disruption Difference Immune Complex Disruption Kit which is designed to dissociate antigen/antibody complexes in serum and plasma using a combination of low pH and heat.

An important aspect of the method of the invention to determine total analyte concentration involves assaying for free analyte at least twice, once in the absence of a spike and at least once in the presence of a known quantity of analyte ("spike") which has been added to the sample. As is shown below, use of an analyte "spike" enables determination of the total concentration of analyte whether free or bound.

Generally, free analyte concentration in a sample is determined "as is" (without use of a spike) in an assay. The same assay is then run at least a second time using a spike. In other words, the sample in the second assay not only contains analyte "as is" but, in addition, also contains a known quantity of analyte ("spike") in addition to whatever analyte was present in the sample. At least one spike must be used in addition to determining analyte concentration in the absence of a spike. It is also possible to use three or more spikes if desired.

Total analyte concentration in the original sample can then be determined from the measurements obtained by calculating the following:

Total Analyte Concentration=Measured Unspiked Sample×Value of Spike/(Measured Spiked Sample—Measured Unspiked Sample).

If two spikes were used (e.g. one at a high level and one at a low level), then the calculation for total analyte concentration would be: Measured Unspiked Sample×(Value of High Spike−Low Spike)/(Measured High Spiked Sample−Measured Low Spiked Sample).

If more than two spikes are used, then these equations can be modified as needed depending upon the number of spikes used.

The following example illustrates the practice of the invention but should not be construed as a limitation thereon.

EXAMPLE 1

Part A: Preparation of Antigen and Antibody Positive Reference Samples

Each of twenty-two antigen and antibody positive reference samples having HIV-1 p24 antigen at a concentration of 194 pg/ml were prepared by mixing 44 μl of an HIV-1 antibody positive, antigen negative serum/plasma with 375 μl of normal human serum/plasma and 45 μl of HIV-1 viral lysate containing 2000 pg/ml p24 antigen.

Part B: Sample Evaluation

Each of the twenty-two reference samples was assayed in the absence and presence of at least one spike. In this evaluation two different spike levels, approximately 200 and 400 pg/ml were used. The Du Pont HIV-1 p24 Core Profile ELISA antigen assay in conjunction with the Du Pont HIV-1 p24 Acid Disruption Difference (ADD) kit described above were used to assay the samples. The ADD kit was used to disrupt antigen/antibody complexes in serum and plasma using a combination of low pH and heat. Samples were acidified with 1.5M glycine reagent, pH 1.85 and were incubated at 37° C. for one hour. After one hour, the samples were neutralized with 1.5M TRIS, pH 11 and were assayed in the Du Pont HIV-1 p24 Core Profile ELISA.

The Du Pont HIV-1 p24 Core Profile ELISA antigen assay utilizes an anti-HIV p24 mouse monoclonal antibody which is immobilized to microtiter plate wells. The immobilized monoclonal antibody then captures HIV-1 p24 antigen released upon lysis of virus in the samples. The captured antigen is complexed with biotinylated polyclonal antibodies to HIV-1 p24 core antigen and probed with a streptavidin-HRP (horseradish peroxidase) conjugate. The complex is then detected by incubation with orthophenylenediamine—HCl (OPD) which produces a yellow color that is directly proportional to the amount of HIV-1 p24 core antigen captured. The absorbance of each well is determined using a microplate reader and calibrated against the absorbance of an HIV-1 p24 core antigen standard curve.

1. Reagents

Glycine Reagent

This is used to acidify sample to about pH 2.0. The Glycine Reagent is 1.5M glycine, pH 1.85

|  | % Comp |
|---|---|
| Glycine | 11.3% |
| HCl | 9.6% |
| Distilled Water | 79.1% |

Tris Reagent

This is 1.5M Tris, pH 11 which is used to neutralize samples after disruption.

|  | % Comp |
|---|---|
| Tris Base | 17.0% |
| Distilled Water | 83.0% |

2. Sample Preparation

The following were added to the wells of a blank microtiter plate:
a) 10 μl of 5% Triton X-100,
b) 90 μl of sample,
c) 10 μl of either negative serum (unspiked), negative serum spiked with approximately 2000 pg/ml HIV-1 p24 antigen (low spike) or negative serum spiked with approximately 4000 pg/ml HIV-1 p24 antigen (high spike).

It should be noted that the actual values of the spike levels were assayed by substituting 90 μl of negative serum for the 90 μl of sample.

3. Assay

90 μl of 1.5M glycine, pH 1.85, and 90 μl of sample or standard were incubated for one hour at 37° C. After one hour, 90 μl of 1.5M Tris pH 11 was added to each well and incubated for ten minutes at room temperature. This sample mixture (150 μl) was then transferred to an HIV-1 p24 Core Profile ELISA plate and incubated for 2 hours at 37° C. The microtiter plate wells were then washed and 100 μl biotinylated detector antibody was added to each well and incubated for one hour at 37° C. The wells were then washed and streptavidin-HRP conjugate at a 1:25 dilution was added, incubated for 15 minutes at 37° C. and the wells were then washed again. OPD substrate was added for thirty minutes at room temperature, the reaction was stopped with kit stop solution (4N sulfuric acid) and the absorbance at 490–650 nm was determined.

4. Determinations

Values for all samples were determined by interpolation from an HIV-1 p24 core antigen standard curve. The actual values of the spikes were determined to be 228 pg/ml (low spike) and 448 pg/ml (high spike) for samples 1–11, and 234 pg/ml (low spike) and 438 pg/ml (high spike) for samples 12–22. As was noted above the actual values of the spike levels were assayed by substituting 90 μl of negative serum for the 90 μl of sample.

Total analyte concentration was determined using each of the following combinations:
a) unspiked sample and low spike;
b) unspiked sample and high spike; and
c) unspiked sample and both low and high spikes.

Determination of Total Antigen Concentration for a single spike was made as follows:

Measured Unspiked Sample×Value of Spike/(Measured Spiked Sample−Measured Unspiked Sample).

Determination of Total Antigen Concentration for both spikes combined was made as follows:

Measured Unspiked Sample×(Value of High Spike—Low Spike)/(Measured High Spiked Sample−Measured Low Spiked Sample)

Total Antigen Concentration Determinations for Sample 1 using data provided in Table 1 and actual spike values provided above are set forth below. The same determinations were made for the remaining twenty-one reference samples.

(a) unspiked sample and low spike $$\frac{50 \times 228 \text{ pg/ml}}{(111 - 50)} = 187 \text{ pg/ml}$$

(b) unspiked sample and high spike $$\frac{50 \times 448 \text{ pg/ml}}{(162 - 50)} = 200 \text{ pg/ml}$$

(c) unspiked sample and both spikes $$\frac{50 \times (448 \text{ pg.ml} - 228 \text{ pg/ml})}{(162 - 111)} = 216 \text{ pg/ml}$$

The results of these calculations are summarized for all 22 samples in Table 2 below.

5. Results

Results are presented in Tables 1 and 2 below. The data presented in Table 1 is the measured HIV-1 p24 antigen level for each sample run in the assay in the absence and presence of both spikes, a low spike and a high spike.

The data presented in Table 2 is the total antigen concentration determined from the data presented in Table 1 and actual values of each spike which were determined as discussed above. A comparison is also set forth between what was actually measured versus total antigen concentration determined. These data show that the presence of an endogenous binding substance, such as an antibody, yields highly inaccurate values for many of the samples when measuring antigen directly in an assay.

The method of the invention overcomes this problem by providing a means to more accurately and precisely determine total analyte concentration in a sample containing analyte in a free and bound form.

TABLE 1

| | Measurement of HIV-1 p24 Antigen In Unspiked and Spiked Samples HIV-1 p24 Antigen, pg/ml | | |
|---|---|---|---|
| Sample | Measured Unspiked Sample | Measured Low Spiked Sample | Measured High Spiked Sample |
| 1 | 50 | 111 | 162 |
| 2 | 35 | 81 | 126 |
| 3 | 79 | 173 | 250 |
| 4 | 32 | 85 | 127 |
| 5 | 57 | 120 | 189 |
| 6 | 49 | 98 | 146 |
| 7 | 46 | 123 | 204 |
| 8 | 175 | 372 | 568 |
| 9 | 124 | 288 | 443 |
| 10 | 175 | 387 | 568 |
| 11 | 215 | 429 | 660 |
| 12 | 192 | 391 | 588 |
| 13 | 202 | 415 | 618 |
| 14 | 164 | 330 | 465 |
| 15 | 146 | 331 | 479 |
| 16 | 183 | 403 | 564 |
| 17 | 137 | 286 | 426 |
| 18 | 185 | 396 | 576 |
| 19 | 205 | 400 | 657 |
| 20 | 199 | 430 | 639 |
| 21 | 197 | 392 | 600 |
| 22 | 173 | 347 | 540 |

TABLE 2

Comparison of Measured Unspiked and Determination of HIV-1 p24 Antigen in Samples Containing 194 pg/ml Using the Method of the Invention Measured Total HIV-1 p24 Antigen Determined Using the Method of the Invention

| Sample | Unspiked | Low Spiked | High Spiked | Both Spikes Combined |
|---|---|---|---|---|
| 1 | 50 | 187 | 200 | 216 |
| 2 | 35 | 173 | 172 | 171 |
| 3 | 79 | 192 | 207 | 226 |
| 4 | 32 | 138 | 151 | 168 |
| 5 | 57 | 206 | 193 | 182 |
| 6 | 49 | 228 | 226 | 225 |
| 7 | 46 | 136 | 130 | 125 |
| 8 | 175 | 203 | 199 | 196 |
| 9 | 124 | 172 | 174 | 176 |
| 10 | 175 | 188 | 199 | 213 |
| 11 | 215 | 229 | 216 | 205 |
| 12 | 192 | 226 | 212 | 199 |
| 13 | 202 | 222 | 213 | 203 |
| 14 | 164 | 231 | 239 | 249 |
| 15 | 146 | 185 | 192 | 201 |
| 16 | 183 | 195 | 210 | 232 |
| 17 | 137 | 215 | 208 | 200 |
| 18 | 185 | 205 | 207 | 210 |
| 19 | 205 | 246 | 199 | 167 |
| 20 | 199 | 202 | 198 | 194 |
| 21 | 197 | 236 | 214 | 193 |
| 22 | 173 | 233 | 206 | 183 |
| Avg. | 137 | 202 | 198 | 197 |
| S.D. | 65 | 30 | 24 | 27 |
| C.V. (%) | 48 | 15 | 12 | 14 |

What is claimed is:

1. A method for determining total analyte concentration in a sample which comprises:
    (a) assaying for the concentration of free analyte in the sample wherein said sample has been subjected to immune complex disruption;
    (b) assaying for the concentration of free analyte in the sample wherein said sample contains a known quantity of analyte which has been added to the sample and further wherein the sample containing the known quantity of analyte has been subjected to immune complex disruption, said determination being made at least once; and
    (c) determining total analyte concentration from the assayed concentrations obtained in steps (a) and (b).

2. A method for determining HIV antigen concentration in a sample which comprises:
    (a) assaying for the concentration of free HIV antigen in the sample wherein said sample has been subjected to immune complex disruption;
    (b) assaying for the concentration of free HIV antigen in the sample wherein said sample contains a known quantity .of HIV antigen which has been added to the sample and further wherein the sample containing the known quantity of HIV antigen has been subjected to immune complex disruption, said determination being made at least once; and
    (c) determining total HIV antigen concentration from the assayed concentrations obtained in steps (a) and (b).

3. A method according to claim 2 where the HIV antigen is HIV-1 p24 antigen.

* * * * *